United States Patent [19]

Benitz et al.

[11] Patent Number: 4,945,086
[45] Date of Patent: Jul. 31, 1990

[54] SMOOTH MUSCLE CELL GROWTH INHIBITOR

[75] Inventors: William E. Benitz; Merton Bernfield, both of Palo Alto, Calif.

[73] Assignee: The Board of Trustees of the Leland Stanford Junior University, Stanford, Calif.

[21] Appl. No.: 189,622

[22] Filed: May 3, 1988

[51] Int. Cl.$^5$ .............................................. C08B 37/10
[52] U.S. Cl. ......................................... 514/56; 536/21
[58] Field of Search ............................ 514/56; 536/21

[56] References Cited

U.S. PATENT DOCUMENTS

| | | | |
|---|---|---|---|
| 4,446,126 | 5/1984 | Jordan | 514/56 |
| 4,698,301 | 10/1987 | Weiss et al. | 514/56 |
| 4,727,063 | 2/1988 | Naggi et al. | 514/56 |
| 4,745,098 | 5/1988 | Michaeli | 514/56 |
| 4,760,131 | 7/1988 | Sundsmo et al. | 514/56 |

OTHER PUBLICATIONS

Nader, H. B.; Dietrich, C. P.; Buonassisi, V.; and Colburn, P., Heparin Sequences in the Heparan Sulfate Chains of an Endothelial Cell Proteoglycan, *Proc. Natl. Acad. Sci. U.S.A.*, (1987), 84: 3565–3569.

Buonassi, V. and Colburn, P., Biological Significance of Heparin Sulfate Proteoglycans, *Ann. N.Y. Acad. Sci.* (1982), 401:76–84.

Castellot, Jr., J. J.; Favreau, L. V. Karnovsky, M. J.; and Rosenberg, R. D., Inhibition of Vascular Smooth Muscle Cell Growth by Endothelial Cell–Derived Heparin, *J. Biol. Chem.* (1982), 257: 11256–11260.

Castellot, Jr., J. J.; Addonizio, M. L.; Rosenberg, R.; and Karnovsky, M. J., Cultured Endothelial Cells Produce a Heparinlike Inhibitor of Smooth Muscle Cell Growth, *J. Cell Biol.* (1981), 90: 372–379.

Gallageher, J. T.; Lyon, M.; and Steward, W. P., Structure and Function of Heparin Sulphate Proteoglycans, *Biochem. J.* (1986), 236: 313–325.

Oohira, A.; Wight, T. N.; and Bornstein P., Sulfated Proteoglycans Synthesized by Vascular Endothelial Cells in Culture, *J. Biol. Chem.* (1988), 258: 2014–2021.

Buonassisi, Sulfated Mucopolysaccharide Synthesis and Secretion in Endothelial Cell Cultures (1973), 76:363–368.

Gamse et al., Metabolism of Sulfated Glycosaminoglycans in Cultured Endothelial Cells and Smooth Muscle Cells from Bovine Aorta (1978), 544:514–528.

Merrilees et al., Interaction of Aortic Endothelial and Smooth Muscle Cells in Culture (1981), 39:147–161.

Castellot et al., Cultured Endothelial Cells Produce a Heparinlike Inhibitor of Smooth Muscle Cell Growth, (1981) 90:372–379.

Chamley-Campbell, What Controls Smooth Muscle Phenotype (1981), 40:347–357.

Buonassisi, Biological Significance of Heparan Sulfate Proteoglycans (1982), 401:76–84.

Oohira et al., Sulfated Proteoglycans Synthesized by Vascular Endothelial Cells in Culture (1983), 257:2014–2021.

Willems et al., Media Conditioned by Cultured Human Vascular Endothelial Cells Inhibit the Growth of Vascular Smooth Muscle Cells (1982), 139:191–197.

Castellot et al., Inhibition of Vascular Smooth Muscle Cell Growth by Endothelial Cell–Derived Heparin (1982), 35:11256–11260.

Shimada et al., Release of Heparan Sulfate Proteoglycans from Cultured Aortic Endothelial Cells by Thrombin (1985), 39:387–397.

Fritze et al., An Antiproliferative Heparan Sulfate Species Produced by Postconfluent Smooth Muscle Cells (1985), 1041–1049.

Gordon et al., Glycosaminoglycan Production in Cultures of Early and Late Passage Human Endothelial Cells: The Influence of an Anionic Endothelial Cell Growth Factor and the Extracellular Matrix (1985), 125:596–607.

Kinsella et al., Modulation of Sulfated Proteoglycan Synthesis by Bovine Aortic Endothelial Cells During Migration (1986), 102:679–687.

Campbell et al., Endothelial Cell Influences on Vascular Smooth Muscle Phenotype (1986), 48:295–306.

Humphries et al., Effects of Hypoxia and Hyperoxia on Proteoglycan Production by Bovine Pulmonary Artery Endothelial Cells (1986), 126:249–253.

Keller et al., Aortic Endothelial Cell Proteoheparan Sulfate (1987), 128:286–306.

Benitz, Control of Proliferation of Pulmonary Vascular Smooth Muscle (May 7, 1987), 3 pages.

Nader et al., Heparin Sequences in the Heparan Sulfate Chains of an Endothelial Cell Proteoglycan (1987), 84:3565–3569.

(List continued on next page.)

Primary Examiner—Ronald W. Griffin
Assistant Examiner—Pamela S. Webber
Attorney, Agent, or Firm—Richard L. Neeley

[57] ABSTRACT

An epithelium-derived inhibitor of the growth of smooth muscle cells is disclosed along with methods for purifying this substance. As initially isolated, the inhibitor comprises a heparan sulfate proteoglycan having a buoyant density of less than 1.4 g/ml which releases a glycosaminoglycan chain having a molecular weight of about 55,000 to 75,000 on protease cleavage. Growth inhibiting activity is found in the glycosaminoglycan chain and in glycosaminoglycan fragments derived therefrom. Use of a dialyzable detergent in purification steps greatly aids in the handling and purification of the inhibitor. The inhibitor can be used in a variety of techniques for inhibiting the growth of smooth muscle cells, both in vivo and in vitro.

29 Claims, No Drawings

OTHER PUBLICATIONS

Cochran et al., "Effect of Heparin on Vascular Smooth Muscle Cells. II. Specific Protein Synthesis", *J. Cellular Physiology* (1985), 36:124–129.

Marcum et al., "Cloned Bovine Aortic Endothelial Cells Synthesize Anticoagulantly", *J. Bio. Chem.* (1986), pp. 1–11.

Clowes, "Kinetics of Cellular Proliferation after Arterial Injury", *Circulation Research* (1986), 58:839–845.

Guyton et al., "Inhibition of Rat Arterial Smooth Muscle Cell Proliferation by Heparin", *Circulation Research* (1980), 46:625–633.

Castellot et al., "Structural Determinants of the Capacity of Heparin to Inhibit the Proliferation of Vascular Smooth Muscle Cells", *J. of Cellular Physiology* (1984), 120:315–320.

Benitz et al., "Heparin Inhibits Proliferation of Fetal Vascular Smooth Muscle Cells in the Absence of Platelet Derived Growth Factor", *J. of Cellular Physiology* (1986), 127:1–7.

Clowes et al., Kinetics of Cellular Proliferation after Arterial Injury (1986), 58:839–845.

Benitz et al., "An Endothelial Cell–Derived Inhibitor of Smooth Muscle Cell Growth has the Characteristics of a Basement Membrane Heparan Sulfate Proteoglycan", *J. Cell. Biol.* (1987), 105:220a.

Benitz et al., "Fetal Pulmonary Arterial Endothelium Produces a Basement Membrane Heparan Sulfate Proteoglycan that Inhibits Smooth Muscle Cell Growth", *Pediatr. Res.* in press (1988).

SMOOTH MUSCLE CELL GROWTH INHIBITOR

Work leading to the present invention was supported in part by grants from the National Institutes of Health, and the government has certain rights in the invention.

INTRODUCTION

1. Field of the Invention

This invention relates to inhibitors or smooth muscle cell growth and to glycosaminoglycans.

2. Background

Smooth muscle cells are specialized muscle cells capable of producing the slower and longer-lasting (in contrast to skeletal muscle) contraction of such tissues as the walls of the stomach, intestines, and blood vessels. For example, a normal artery wall consists of a single continuous layer of endothelial cells lining the lumen of the artery, a layer of smooth-muscle cells arranged in either a single layer (as in small muscular arteries) or multiple lamella (as in elastic arteries), and an outer external coat consisting of collagen bundles, elastic fibers, smooth-muscle cells, and fibroblasts.

Maintenance of this defined artery structure is an important health consideration. The proliferation of smooth muscle cells after endothelial cell injury has been postulated to be a key step in the early pathogenesis of arteriosclerosis (Ross and Glomset, *Science* (1973) 180:1332-1339). Some studies have shown smooth muscle cell inhibition activity for both anticoagulant heparin (Clowes and Karnovsky, *Nature* (1977) 265:625-626), and non-anticoagulant heparin (Guyton et al., *Circ. Res.* (1980) 46:625-634). More recent studies from the same laboratories have discussed various structures of heparin that appear to be essential to the inhibition of the proliferation of vascular smooth muscle cells. See, for example, Castellot et al., *J. Cell. Physiol.* (1984) 120:315-320. A heparin-like inhibitor of smooth muscle cell proliferation secreted systemically by endothelial cells has also been reported. See, for example, Castellot et al., *J. Cell Biol.* (1981) 90:372-379.

However, studies in the laboratories of the present inventors have indicated that the heparin molecules used in prior studies do not appear to be the natural molecule that controls growth of smooth muscle cells and therefore will not represent the optimal molecule for therapeutic use. Additional smooth muscle cell growth inhibitors and methods of obtaining them therefore continue to represent desirable goals of medical and biochemical research.

SUMMARY OF THE INVENTION

Accordingly, the present invention provides an endothelium-derived smooth muscle cell growth inhibitor comprising a substantially pure glycosaminoglycan or heparan sulfate proteoglycan. The inhibitor has smooth muscle cell growth inhibition activity and is isolatable from endothelial-cell-conditioned media as all or part of a heparan sulfate proteoglycan having a buoyant density of less than 1.4 g/ml and which releases a glycosaminoglycan chain having a molecular weight of about 55,000 to 75,000 on protease cleavage. The inhibitor of the invention can be presented either as an intact proteoglycan, as an intact glycosaminoglycan chain, or as a fragment retaining inhibitor activity. The invention also comprises a technique for isolating this endothelium-derived proteoglycan and glycosaminoglycan in which a key step is adding a dialyzable detergent to the medium from which the glycosaminoglycan (as a proteoglycan) is being isolated.

DESCRIPTION OF SPECIFIC EMBODIMENTS

The present invention arose in part out of studies showing the ability of endothelial-cell-conditioned media to inhibit the growth of smooth muscle cells in cultures. Further studies have indicated that the active factor is a glycosaminoglycan isolatable from a heparan sulfate proteoglycan secreted by endothelial cells. The proteoglycan, when subjected to protease cleavage, releases glycosaminoglycan chains having a molecular weight of about 55,000 to 75,000, usually about 60,000 to about 70,000 as measured by size exclusion chromatography. These initially released chains are referred to as "glycosaminoglycan chains" in this specification to distinguish them from the broader reference to an active "glycosaminoglycan" of the invention, which can be either an entire glycosaminoglycan chain as released from the proteoglycan or a fragment of the glycosaminoglycan chain having smooth muscle cell growth inhibition activity. Cleavage of the initially released glycosaminoglycan chain into smaller fragments retaining inhibitor activity is readily accomplished due to the repeating nature of the subunits found in glycosaminoglycan chains.

The purification techniques described later in the specification allow purification of the inhibitor of the invention from endothelial-cell-conditioned media obtained from the culture of endothelial cells from a variety of sources. The endothelial cells are typically mammalian (especially primate) and often are human, porcine, bovine, sheep, rabbit, rat, mouse, or monkey endothelial cells. The cells can be obtained from any tissue or organ containing endothelial cells. Organs and tissues rich in endothelial cells, such as blood vessels and lungs, represent preferred sources. The cells may be obtained directly from the animal of origin (typically from a slaughterhouse) or may be used after culture of a tissue- or cell-culture line. For example, endothelial cells cultured from the pulmonary arteries of near-term bovine fetuses represent a useful source of endothelial cells. Endothelial cells for long-term cell culture are commercially available from a variety of sources, such as the American Type Culture Collection, Rockville, Md.

Endothelial cells are cultured in a medium capable of sustaining their growth. Numerous suitable media are discussed in the scientific literature, while others are available commercially. Examples of commercial media suitable for the growth of endothelial cells include Dulbecco's modification of Eagle's medium (DMEM); Eagle's minimum essential medium (MEM; typically used with serum supplement); Ham's F10, F12, F12M, F12K, and MCDB101-104; and MCDB107. The standard medium generally is supplemented with a source of serum protein, typically 10% fetal calf serum (FCS). Culture conditions generally provide a humidified atmosphere of 95% air and 5% carbon dioxide at 37° C. Cell culture usually takes place in two stages: propagation and maintenance. Suitability of any growth medium or modification thereof for propagation of cell cultures can be ascertained by comparison of its ability to support proliferation of sparsely plated (5,000 to 25,000 cells/cm$^2$) endothelial cells. Suitability of any medium for maintenance of confluent endothelial cell cultures can be assessed by microscopic inspection of the endothelial cell cultures over several days in culture. Suitable media allow maintenance of a typical "cobblestone" phenotype (described in Strike et al., *Methods in Cell Biology* (1980) 21A:135-151), in which the cells have close lateral appositions and are present only in a single layer. Optimal media allow maintenance of this phenotype for at least two weeks after cultures achieve confluence. A conditioned medium is one that has been used for the maintenance of confluent cells, usually for at least 24 hours, preferably at least 72 hours, in order to increase the concentration of inhibitor in the medium.

The growth inhibitor is initially present in an endothelial-cell-conditioned medium as a heparan sulfate proteoglycan typically having a molecular weight of about $10^5$ to about $10^7$, usually about $5 \times 10^5$ to about $2 \times 10^6$, especially about $10^6$, as measured by size exclusion chromatography, and a buoyant density of less than 1.4 g/ml, usually about 1.3. The proteoglycan exhibits smooth muscle cell growth inhibition activity which is not destroyed by the enzyme protease, which cleaves the protein portion of the molecule. Protease cleavage releases a glycosaminoglycan chain having a molecular weight of about 55,000 to 75,000, usually about 60,000 to 70,000, having the growth inhibitor activity. The proteoglycan binds specifically with an antibody having specific binding affinity for a protein epitope of a basement membrane heparan sulfate proteoglycan, indicating a similarity in structure to such molecules. For example, the prototypic basement membrane heparan sulfate proteogylcan produced by the Engelbreth-Holm-Swarm (EHS) tumor can be used to raise antibodies which are cross-reactive with the endothelial-cell-derived proteoglycan of the invention. The EHS tumor line is widely disseminated and is available from a variety of sources, including The National Institute of Dental Research, Bethesda, Md (Dr. George Martins). Other characteristics of the proteoglycan of the invention include solubility in liquid cell culture media as an intact proteoglycan in the presence of albumin or serum. Some (but not all) other proteoglycans are not soluble but are bound to cell surfaces under the same conditions. Growth inhibitor activity is destroyed by prolonged treatment with nitrous acid, heparinase, or heparitinase or by other treatments that destroy glycosaminoglycan chains. The glycosaminoglycan of the invention is estimated to be $10^4$ to $5 \times 10^4$ times as active (on a weight basis) as native commercial, anticoagulant heparin in inhibiting smooth muscle cell growth.

The glycosaminoglycan of the invention belongs to a class of compounds, formerly known as mucopolysaccharides, consisting of long, unbranched polysaccharide chains containing repeating disaccharide units. The glycosaminoglycan has been classified as a heparan sulfate. Heparan sulfates principally contain a repeating disaccharide unit that can be expressed by the formula (A-B)n, in which A and B represent monosaccharides and n represents the number of repeating units. The A unit is typically D-glucuronic acid or L-iduronic acid (the epimer of D-glucuronic acid at the position where the carboxyl group is located) and the B unit is typically N-acetyl-D-glucosamine. D-galactose and D-xylose are also typically present at the linkage of the glycosaminoglycan glycan to the core protein. The number of sulfates per disaccharide unit is typically from about 0.2 to about 3, more often about 1 to 3 or 1.5 to 3. The sulfates are present either as sulfate esters of hydroxy groups on the sugar or as N-sulfated glycosamine. Heparan sulfates resemble heparin in that they contain a similar selection of sugars but differ in that they contain a different proportion of glucuronic acid residues and a different extent of N-sulfation. For a brief review of the structure of heparan sulfates and their relation to other glycosaminoglycans, see Cifonelli and King, *Biochemistry* (1977) 16:2137-2141, Hurst and Settine, *Anal. Biochem.* (1981) 115:88-92, and Gallager, Lyon, and Steward, *Biochem. J.* (1986) 236:313-325.

The inhibitor of the invention can comprise either a proteoglycan as secreted by endothelial cells or the glycosaminoglycan chain released therefrom by protease or other enzymatic or chemical cleavage. Additionally, limited cleavage of the heparan sulfate glycosaminoglycan chain with a reagent such as nitrous acid (the prototypic reagent used to cleave heparan sulfate chains) produces a series of fragments of lower molecular weight, typically from about 500 daltons (the approximate weight at a disaccharide unit) and ranging in multiples of about 500 (i.e., multiple disaccharide units) to full-length chains. Glycosaminoglycan chains can also be fragmented using enzymes such as heparinase or heparitinase. Either mixtures of such cleaved fragmentsor-fractions obtained from cleaved mixtures (e.g., fractions based on separation into di-, tetra-, hexa-, octa-, etc., saccharides by size exclusion chromatography) are within the scope of the present invention as long as the requisite smooth muscle cell growth inhibition activity is present. Such activity can easily be measured using the assay described in the specific examples that follow.

Since glycosaminoglycans are heterologous, it is not possible to define specifically the entire structure of a glycosaminoglycan of the invention. However, a glycosaminoglycan or proteoglycan of the invention can be recognized by its relationship to the original endothelial cell-conditioned medium described above and the proteoglycan contained therein. However, analysis of glycosaminoglycan fragments will provide sufficient information to allow chemical synthesis of small, active glycosaminoglycans (or isolation of such fragments from other sources). Such materials, although not "isolated" from the heparan sulfate proteoglycan of its invention nevertheless are "isolatable" therefrom and fall within the scope of the present invention. Because they can be obtained easily by the purification techniques described herein, proteoglycans, glycosaminoglycan chains, and smaller glycosaminoglycans directly isolated from the initially released heparan sulfate proteoglycan of the invention are preferred.

Because of their heterogeneity, proteoglycans and glycosaminoglycans are extremely difficult to purify and/or isolate, at least in the sense of purifying to provide a composition containing only one molecular structure. Accordingly, "pure" when used in this specification refers to a composition in which the proteoglycan, glycosam-inoglycan, or mixture of the invention comprises at least 99 weight % of similar molecules (i.e., other proteoglycans and glycosaminoglycans and fragments derived from such molecules) and preferably at least 99 weight % of other high-molecular-weight molecules (more preferably greater than 99.5%) present in a composition containing the inhibitor. High molecular weight preferably is at least 500K when referring to proteoglycans and at least 10K when returning to glycosaminoglycan chains. The composition can contain water and other small molecules of low molecular weight (preferably less than 1000, more preferably less than 500), such as buffer or the like. "Substantially pure" refers to a composition that can contain other macromolecules but which exhibits smooth muscle cell growth inhibition activity at a level (on a weight basis) at least 3 times, preferably 5 times, that of an endothelial-cell-conditioned medium and 10 times, preferably 100 times, that of an equal weight of commercial beef heart heparin (e.g., commercial heparin having an anticoagulant activity of about 120 USP units/mg). Preferably, substantially pure refers to at least 50% by weight pure, more preferably at least 80% by weight pure, and even more preferably at least 90% by weight pure.

It will be recognized that numerical limits and other specific limits on various characteristics of the proteoglycans and glycosaminoglycans of the invention can be independently selected to provide groupings of intermediate preference, even if a limit was expressed originally as one limit of a range. For example, glycosaminoglycan chains of molecular weight 55,000 to 70,000 represent one such grouping that can be selected. Different characteristics, such as molecular weight and source of endothelial cells, can likewise be combined to provide combinations of the invention even if the characteristics are not originally mentioned together.

It will also be recognized that test numerical limits are derived in most part from experimental data and therefore are subject to the precision of the experimental method. Because of the different degrees of precision that exist for different measuring techniques, a number will have different precisions for different parameters. However, its meaning will be readily understood by one skilled in the art who commonly uses the characteristic to define the properties of a substance in question. Therefore, equality with a number means that no significant difference exists.

The word "about" represents a larger difference than the minimum recognizable difference as determined by the precision of the measurement. Usually "about" means less than 10, preferably less than 5, more preferably less than 2, times the minimum experimentally determinable difference using standard techniques available in May 1988.

The present invention also provides a method of purifying a glycosaminoglycan or proteoglycan smooth muscle cell growth inhibitor from a medium containing the inhibitor as biochemically synthesized by endothelial cells. Initial attempts to isolate the proteoglycan and glycosaminoglycan of the invention were unsuccessful because of the tendency of the proteoglycan core protein to stick to surfaces of the vessels in which purification was taking place. However, the present inventors have discovered that by including a dialyzable detergent in the medium from which the proteoglycan is to be isolated and maintaining the detergent in the presence of the proteoglycan during purification steps, purification can take place without excessive loss of product. For example, typical purification techniques such as gel filtration, density gradient centrifugation, and ion exchange chromatography can be carried out in the presence of detergent to provide the desired product, while the same steps carried out in the absence of detergent do not lead to the desired product.

Biological detergents that can be used in the practice of the invention are readily available from commercial sources. For example, both the Sigma and Aldrich catalogs of chemical and biochemical reagents list numerous detergents that can be used in biological circumstances. Octylglucoside is a particularly preferred detergent. Other dialyzable detergents include sodium deoxycholate; 3-(3-cholamidopropyl)dimethylammonio-1-propanesulfonate (CHAPS); hexyl-, heptyl-, octyl-, nonyl-, and decyl-$\beta$-D-glucopyranoside; heptyl- and octyl-$\beta$-D-thioglucopyranoside; and octanoyl-, nonoyl-, and decanoyl-N-methylglucamide (e.g., MEGA-8, MEGA-9, and MEGA-10 from Omega Corp.). Other detergents can be readily tested for operability in this aspect of the invention by including detergent at 1 to 5 times its critical micellular concentration in a solution containing an inhibitor of the invention, dialyzing the sample detergent against culture medium or buffered saline in dialysis tubing with a molecular weight cutoff of $5 \times 10^3$ to $500 \times 10^3$ (preferably no more than $250 \times 10^5$, even more preferably no more than $100 \times 10^3$) and determining whether smooth muscle cell growth inhibitor activity is recoverable from the dialyzed sample.

For example, urea and octylglucoside can be added to an endothelium-conditioned medium to provide final concentrations of about 5–7 M and 1–2 g/ml, respectively. This medium is loaded onto an ion exchange column which is then washed in a typical manner. Elution with a sodium chloride gradient provides a purified proteoglycan of the invention.

Alternatively, octylglucoside (as above), guanidine, and cesium chloride can be subjected to isopycnic density gradient ultracentrifugation to obtain a purified fraction having an initial buoyant density of about 1.3 g/ml.

As a third purification technique, a buffered solution of conditioned medium containing octylglucoside can be subjected to gel filtration to separate molecules according to molecular weight.

These purification steps can be combined if desired, with a preferred sequence comprising ion exchange followed by gradient centrifugation followed by gel filtration.

A stabilizing protein, usually serum or albumin, is typically added to the sample prior to removal of the detergent or release of the glycosaminoglycan from the proteoglycan, whichever comes first. For example, serum at a concentration of 1–20%, preferably about 10%, is satisfactory. Sample can be dialyzed against buffered saline to remove detergent, at which time inhibitor activity can be assessed in a bioassay.

Endothelium-derived inhibitors of the invention can be used in a variety of techniques for the purpose of inhibiting growth of smooth muscle cells. The method will typically comprise adding a growth inhibiting amount of an epithelium-derived inhibitor of the invention to a medium containing smooth muscle cells, whether in vivo or in vitro.

A typical in vitro application is in the growth of endothelial cells from natural sources. It is difficult to separate endothelial cells from smooth muscle cells, and an inhibitor of the invention can be added to the growth medium to prevent smooth muscle cells from overgrowing the culture. The inhibitor is typically added in an amount to provide a concentration in the medium of from about 20 to about 1000 ng/ml, preferably 50 to 250 ng/ml. The amount necessary can be adjusted as desired in response to the growth conditions in the culture medium.

A typical in vivo operation would be administration of an inhibitor of the invention to a mammal, typically a human. In such cases, the "growth medium" to which the composition of the invention is being added is an artery or vein. When administered to a mammal, the amount of inhibitor is generally sufficient to provide a concentration of from 50 to 500 ng/ml. In an adult human, an effective dose range is expected to be 5 to 50, preferably 10 to 25 μg/patient/day. Administration by a method that provides an intact glycosaminoglycan or proteoglycan of the invention to the arterial or veinous wall is preferred, typically intravenous administration. Subcutaneous, intramuscular, and oral administration are also possible, especially for glycosaminoglycans.

The invention now being generally described, the same will be better understood by reference to the following detailed description which is provided for purposes of illustration only and is not to be considered limiting of the invention unless so specified.

EXAMPLES

Abbreviations

CPC =Cetyl pyridinium chloride; DMEM=Dulbecco's modified Eagle medium; EC=Endothelial cells; EHS=Englebreth-Holm-Swarm; FCS=Fetal calf serum; GAG=Glycosaminoglycan; PG=Proteoglycan; SMC=Smooth muscle cells; TBS=Tris-buffered saline.

Materials and Methods

Cell Culture

Smooth muscle cells (SMC) were cultured from the main pulmonary arteries of near-term bovine fetuses by the explant method of Ross, *J. Cell Biol.* (1977) 50:172-186, and characterized by phase and electron microscopy. Smooth muscle cells were used for experiments only in the second to fourth passage after harvest from the primary culture. Endothelial cells (EC) were cultured from the pulmonary arteries of near-term bovine fetuses and characterized by phase and electron microscopy and by staining with anti-Factor VIII antibody and acetyl low-density lipoprotein. Factor VIII antigen (a coagulation factor) is produced exclusively by endothelium. Acetyl low-density lipoprotein binds selectively to specific receptors present on endothelial cells but not on other cell types. These are therefore useful in confirming the identity of cultured endothelial cells. Culture of SMC and EC is described in Benitz et al., *Pediatr. Res.* (1986) 20:966-972. EC were used for experiments only in the second or third passage after harvest from primary culture Primary cultures were harvested by rinsing the monolayer with a buffer containing 20 mM Tris, 140 mM NaCl, and 0.5 mM EDTA (pH 7.4) and releasing the cells by digestion for 3 to 5 min with trypsin(1:250, NF; 0.5 g/1)-EDTA(0.5 mM) diluted 1:2 to 1:3 with Tris-NaCl-EDTA Cells were used immediately for experiments or placed in 10% dimethylsulfoxide in fetal calf serum (FCS; Tissue Culture Biologicals, Tulare, CA) to be frozen in liquid nitrogen. The standard medium for all cultures and experiments were Dulbecco's modified Eagle medium (DMEM; GIBCO, Grand Island, N.Y.) with 2 mM glutamine, 10 U/ml penicillin, and 10 μg/ml streptomycin. Stock cultures were maintained in standard medium supplemented with 10% FCS. All cultures were incubated in a humidified atmosphere of 95% air and 5% CO2 at 37° C.

Preparation and Metabolic Labeling of Conditioned Medium

Medium supplemented with 10% FCS was conditioned for 48 hrs over endothelial cell cultures which had been confluent for at least 3 days. Conditioned medium was collected, centrifuged (1200 g for 3 min) to remove cells and particulate material, and either used immediately or frozen for use within 60 days. Confluent monolayers of EC in 100 mm culture dishes were labeled in 8 ml of DMEM with 10% FCS containing 100 μCi/ml of carrier-free $H_2{}^{35}SO_4$ (New England Nuclear, Boston, MA) for 48 hrs. Metabolically labeled medium was collected and stored as described above. The endothelial cell layer was rinsed twice with Puck's balanced salt solution and labeled glycosaminoglycans (GAG) and proteoglycans (PG) were extracted into 2% SDS in Puck's balanced salt solution.

Growth Inhibition Assay

Growth inhibitor activity was assessed using a previously published SMC growth assay (Benitz et al., *J. Cell Physiol.* (1986) 127:1-7). Briefly, SMC were plated at 25,000 cells/35 mm dish in DMEM with 10% FCS and allowed to attach for 4 to 6 hrs. The plating medium was then removed and experimental medium or control (unconditioned) medium was added to triplicate or quadruplicate dishes. Several dishes were frozen as zero time samples. After 6 days of incubation, the DNA contents of all samples were determined using a Hoechst 33258 spectrofluorimeter. The extent of growth inhibition was calculated from the equation:

$$\% \text{ Inhibition} = 100 - \frac{\text{Net growth in experimental medium}}{\text{Net growth in control medium}} \times 100$$

Analysis of $^{35}SO_4$-labeled Materials

Radiosulfate-labeled materials were analyzed by blotting samples onto Watmann 3 mm paper filters impregnated with cetyl pyridinium chloride (CPC). After drying the filters were washed twice in water, soaked for 1 hr in 25 mM sodium sulfate, and washed again in water. These steps remove free sulfate and other materials which are soluble in the presence of CPC (including sulfated oligosaccharides produced by degradation of GAG), but GAG-containing materials are retained on the filter. Subsequent extraction of the filters with 10% trichloroacetic acid quantitatively removes free GAG but fails to remove PG. Following these treatments, the filters were rinsed once with 95% ethanol, dried, and subjected to scintillation counting. This procedure allows rapid quantitation of the $^{35}SO_4$-labeled GAG and PG in these samples. Alternatively, unincorporated $^{35}SO_4$ was removed from samples of radiolabeled conditioned medium by buffer exchange on Sephadex G-100, an incorporation of $^{35}SO_4$ into macromolecules was assessed by scintillation counting in Aquamix (ICN Radiochemicals, Irvine, Calif.).

Enzymatic and Chemical Digestions

Media were treated with Flavobacterium heparin lyase (Heparinase; Miles, Elkhart, Ind.) at 0.5 U/ml for 1 hr at 37° C; residual enzyme activity was destroyed by boiling for 10 min. Conditioned and unconditioned media were treated with 0.4 mg/ml Streptomyces protease (Calbiochem-Behring, La Jolla, Calif.) at 37° C. After 12 hrs, additional protease (0.2 mg/ml) was added to each sample, and the digestion was continued for an additional 12 hrs. The samples were then boiled for 15 min and sterilized by filtration through 0.22 μm filters. Treatment of medium with chondroitin ABC lyase (Chondroitinase ABC; Miles, Elkhart, Ind.) was carried out at an enzyme concentration of 0.05 U/ml at 37° C for 3 hrs and was terminated by boiling for 10 min. Nitrous acid digestions were performed with 0.24 M NaNO$_2$ in 1.5 M acetic acid (pH 2) at room temperature for 90 min, before addition of ammonium sulfamate to stop the reaction. The nitrous acid digests were neutralized with NaOH and dialyzed in 6000–8000 dalton molecular weight cutoff dialysis tubing (SpectraPor, Los Angeles, Calif.) against 30% polyethylene glycol (15–20,000 flake) in 10 mM Tris, 140 mM NaCl, to return the samples to their starting volume. The products of these digestions were then reconstituted for bioassay by exhaustive dialysis against DMEM (5 changes over 4 days). In most cases, fresh FCS (10%) was also added to each sample. One mg/ml bovine serum albumin (Sigma, St. Louis, Mo.) was added to protease-treated samples that were not supplemented with serum; this was necessary to maintain attachment of SMC to the culture plates during the growth inhibition assay.

For PG analyses, pooled fractions prepared from metabolically labeled medium by density gradient ultracentrifugation were dialyzed against a buffer containing 50 mM Tris, and 30 mM sodium acetate (pH 8.0) with 0.1% Triton X-100 and digested with 0.15 U/ml chondroitinase ABC at 37° C for 3 hrs. Additional enzyme (0.15 U/ml) was then added and the digestion continued for one additional hour. Aliquots of these digests were further treated with 100 mM NaOH under reducing conditions (1 M KBH$_4$) at 37° C. for 20 hrs, followed by neutralization with acetic acid to pH 5.5, or with nitrous acid as described above.

Ion Exchange Chromatography

EC-conditioned medium was adjusted to 6 M urea and 50 mM n-octylglucopyranoside or 0.5% Triton X-100 and loaded onto DEAE-Sephacel pre-equilibrated with buffer A (6 M urea, 50 mM Tris, 10 mM EDTA, 200 mM NaCl, at pH 7.4). The column was washed with buffer A and then eluted with an NaCl gradient from 200–800 mM in the same buffer. The salt concentration in each fraction was determined by measurement of conductivity (CDM 80 conductivity meter, Radiometer, Copenhagen).

Buoyant Density Ultracentrifugation

Pooled fractions from density gradients were buffer exchanged into 4 M guanidine HCl, 150 mM NaCl, 50 mM Tris, 10 mM EDTA with 50 mM n-octylglucopyranoside or 0.5% Triton X-100 (pH 7.4) by ultrafiltration using a filter with a nominal molecular weight cutoff of 5000 daltons (YM-5, Amicon), then adjusted to a final density of 1.3 g/ml by addition of crystalline cesium chloride. A small amount of $^{35}SO_4$-labeled macromolecules from EC-conditioned medium (approximately 200,000 cpm of the pooled $V_0$ fractions from Sephadex G-100) was added to allow assessment of the distribution of GAG and PG. Gradients were formed by centrifugation using an SW-65 rotor in an L8-70M centrifuge (Beckman, Palo Alto, Calif.) at 46,000 rpm for 48 hrs at 15° C. Gradients were fractionated and the radioactivity profile was determined by scintillation counting, as described above. The density profile was determined by weighing aliquots. Fractions were pooled and reconstituted for bioassay by addition of FCS (10%) and dialysis in 6000–8000 dalton molecular weight cutoff tubing against several changes of phosphate (10 mM) buffered saline (140 mM NaCl), followed by exhaustive dialysis against DMEM at 4° C.

Each pooled sample was then brought to the starting volume of the conditioned medium used in the preparation by addition of DMEM and FCS (to final concentration of 10%).

Gel Filtration Chromatography

Pooled fractions from cesium chloride gradients were digested with chondroitinase ABC. Aliquots were taken for gel filtration or for further treatment with alkali or nitrous acid, as described above. All samples were adjusted to 15 SDS and 50 mM Tris (pH 8.0) prior to application to the column. Size exclusion chromatography was performed at room temperature on columns (0.8×25 cm) of Sepharose CL-4B (Pharmacia, Piscataway, N.J.) eluted with 1% SDS, 150 mM NaCl, 50 mM Tris buffer (pH 8.0) at 0.1 ml/min. Aliquots of eluted fractions were taken for scintillation counting in Aquamix (Westchem, San Diego, Calif.) using an LS-2000 scintillation counter (Beckman, Palo Alto, Calif.). The void volume ($V_O$) and the total included volume ($V_T$) were determined using blue dextran T-2000 (Sigma, St. Louis, Mo.) and vitamin B$_{12}$ (Sigma, St. Louis, Mo.), respectively, as markers. Molecular weights were estimated by the $K_{av}$ method.

Immunodot Assay

Solid-phase immunodetection of PGs was performed using a wet cationic nylon membrane (Gene-Trans; Plasco, Woburn, Mass.) placed in an immunodot apparatus (Bio-Rad, Richmond, Calif.). Samples from cesium chloride gradients were diluted to a final chloride concentration less than 0.2 M and all samples were adjusted to 8 M urea and buffered to pH 4.5 with 50 mM acetate before loading onto the membrane using mild vacuum The membrane was then removed from the manifold and rinsed once with acetate buffered saline (50 mM acetate, 150 mM NaCl, pH 4.5) and twice with 20 mM Tris, 140 mM NaCl at pH 7.2 (TBS) with 0.1% Tween-80. The membrane was incubated overnight with an antiserum (designated BM-1) raised against the basement membrane heparan sulfate PG of the Engelbreth-HolmSwarm (EHS) tumor diluted 1:625 in TBS, then for 30 min at room temperature with peroxidase-conjugated goat anti-rabbit IgG (CALTAG, South San Francisco, Calif.) diluted 1:1500 in TBS with 1% FCS. The BM-1 antiserum can be obtained from the National Institutes of Dental
, Bethesda, Md. (Dr. John Hassell), or an Research equivalent antiserum can be prepared using standard techniques of immunology and the EHS basement membrane heparan sulfate proteoglycan (as an immunogen). The immobilized peroxidase conjugate was visualized with 4-chloro-1-naphtol (0.05% w/v) and hydrogen peroxide (0.03% v/v) in TBS.

Statistical Methods

The DNA content or percent inhibition of growth for each group of samples is expressed as the mean ±standard deviation for at least 3 dishes. DNA contents were compared by one-way analysis of variance. Selected pairs of sample means were compared using Student's unpaired two-tailed t test. The Bonferroni correction was applied whenever such t tests were utilized in multiple comparisons. Significance was assumed at $P<0.05$.

Results

Conditioned Medium Contains a Heparin-like Inhibitor of SMC Growth

The increment in the DNA content of sparsely plated SMC cultures incubated with EC-conditioned medium for 6 days was only 53% of that in control cultures incubated with unconditioned medium (P<0.005). Protease treatment completely destroyed the ability of both conditioned and unconditioned medium to support SMC proliferation (P<0.005). SMC growth was completely restored to control levels in protease-treated control medium supplemented with fresh FCS (10%), but was markedly reduced in similarly supplemented EC-conditioned medium (P<0 005). Addition of fresh DMEM (1:1) or exhaustive dialysis against DMEM followed by supplementation with FCS (10%) also failed to abolish the growthinhibiting effects of EC-conditioned medium. These results confirm that growth of SMC from the fetal pulmonary arteries requires polypeptide factors present in serum, and indicate that reduced growth of SMC in medium conditioned by cultured EC is not due to removal of serum factors or medium constituents. In addition, the EC-derived inhibitor of SMC growth resists protease digestion and destruction by boiling for 15 min (with or without prior protease treatment), indicating that it is not a polypeptide.

Inhibition of SMC growth by EC-conditioned medium was reduced, but not completely eliminated, by treatment of the medium with heparinase (P<0.015). Heparinase treatment had no effect on proliferation of SMC in control (unconditioned) medium, but did reverse the inhibitory effects of heparin (100 $\mu$g/ml) on SMC proliferation (P<0.01). Treatment of EC-conditioned medium with Streptomyces protease resulted in increased growth inhibiting activity (P<0.01). The inhibitory activity of this protease-digested EC-conditioned medium was markedly reduced after treatment with nitrous acid (P<0.01), which selectively cleaves heparin and haparan sulfate. Treatment with chondroitinase ABC, which digests chondroitin-4-sulfate, chondroitin-6sulfate, and dermatan sulfate, had no effect on growth inhibition. These results indicate the cultured EC from fetal calf pulmonary arteries produce a heparan sulfate or heparin-like inhibitor of SMC proliferation.

Kinetics of $^{35}SO_4$ Incorporation into Glycosaminoglycan

Endothelial cell cultures were metabolically labeled with carrier-free $^{35}SO_4$ (100 $\mu$Ci/ml) for intervals ranging from 0 to 48 hrs. Incorporation of $^{35}SO_4$ into GAG and PG of the medium or cell layer (which included both the EC and their extracellular matrix) was assessed using the CPC filter assay. For each of these samples, more than 95% of the CPC-precipitable $^{35}SO_4$ resisted extraction from the filters into 10% trichloroacetic acid, indicating that very little free GAG was present. Radiolabeling of PG reached a steady-state in the cell layer at approximately 16 hrs, but there was linear accumulation of radiolabeled PG in the medium for at least 48 hrs. Digestion of aliquots of $^{35}SO_4$-labeled medium with nitrous acid or chondroitinase ABC prior to blotting onto CPC-impregnated filters demonstrated that approximately 40% of the CPC-precipitable label in the medium is in heparan sulfate and 60% is in chondroitin or dermatan sulfate. Thus, pulmonary arterial EC release heparan sulfate PG into their culture medium.

Buoyant Density Fractionation

Ultracentrifugation of EC-conditioned medium under dissociative conditions in cesium chloride for 72 hrs resulted in formation of a density gradient from ca. 1.2 to 1.7 g/ml. CPC-precipitable $^{35}SO_4$ label was recovered in fractions of intermediate density, with a modal density of 1.3 g/ml and a broad peak of higher density, ranging up to 1.5 g/ml. After protease digestion of the conditioned medium, CPC-precipitable $^{35}SO_4$ label was recovered only in the high density (>1.6 g/ml) fractions. This result indicates that the $^{35}SO_4$-labeled material in EC-conditioned medium is PG, from which GAG chains are released by protease treatment After determination of the distribution of the CPC-precipitable radioactivity, fractions from the gradients were combined into 4 pooled fractions of equal size (numbered I-IV). Controls consisted of identically prepared fractions from unconditioned medium. Growth inhibiting activity was recovered in the lowest density pool (fraction IV, density 1.2 to 1.35 g/ml), in which the radiolabeled PG was present at a modal buoyant density of 1.3 g/ml. Growth in medium prepared from EC-conditioned medium fractions I, II, and III was not significantly different from that in controls.

Gel Filtration Chromatography

Pooled fraction IV from the cesium chloride gradient was dialyzed against chondroitin ABC lyase buffer with 0.1% Triton X-100 and digested with chondroitin ABC lyase. Aliquots of this preparation were subjected to gel filtration on Sepharose CL-4B, and elution of $^{35}SO_4$-labeled materials was assessed by scintillation counting. The $^{35}SO_4$ label eluted in two peaks, one at a Kav or 0.03 to 0.07 (barely included in the column) and the other at the Vt. After alkaline digestion, the high molecular weight peak shifted to a Kav of 0.45 to 0.50, confirming the that GAGs were attached to a core protein. After digestion with nitrous acid, $^{35}SO_4$-label eluted only at Vt., indicating that the peaks eluting at Kav of 0.03 to 0.07 and 0.45 to 0.50 consisted of heparan sulfate. Thus, pooled fraction IV contains a heparan sulfate PG with an overall molecular weight of ca. $10^6$ daltons. By comparison with the elution positions of chondroitin sulfate clusters of known molecular weight, the molecular weight of the haparan sulfate chains is estimated to be 60,000 to 70,000 daltons.

Immunoblotting

Because the haparan sulfate PG released by fetal pulmonary arterial EC was similar in overall size, GAG chain size, and buoyant density to the low density basement membrane heparan sulfate PG of the EHS tumor (e.g., Hassell et al., *J. Biol. Chem.* (1985) 260: 8098-8105), crossreactivity with the BM-1 antiserum raised against this EHS tumor PG was tested. Immunoblotting of individual fractions from the cesium chloride gradients demonstrated codistribution of BM-1 immunoreactivity with the growth inhibiting activity. Aliquots of pooled fraction IV also exhibited reactivity with the BM-1 antiserum in this assay. In this assay, the GAG chains bind the PG to the membrane, but the GAG-free core protein is not retained. After alkaline treatment of fraction IV, the $^{35}SO_4$ label was retained on the membrane, but immunoreactivity was lost, indicating that the BM-1 antibody reacts with the core protein of the EC-derived PG. After treatment with nitrous acid, however, radioactivity retained on the cationic membrane was reduced and immunoreactivity was lost, indicating that inability to immobilize the heparan sulfate PG antigen on the membrane results in loss of immunoreactivity. Thus, the BM-1 antiserum reacts with the core protein of the heparan sulfate (but not with the chondroitin sulfate) PG produced by EC cultured from the fetal bovine pulmonary artery. These results indicate that the EC-derived inhibitor of SMC growth shares the a number of characteristics of the basement membrane heparan sulfate PG of the EHS tumor, as shown in the following Table.

| Endothelium-Derived Growth Inhibitor is a Basement Membrane Proteoglycan | | |
|---|---|---|
| Characteristic | Endothelial Medium HSPG | EHS Tumor Basement Membrane HSPG |
| Overall Size (daltons) | −1,000,000 | 750,000 |
| GAG Chain Size | 65,000 | 65,000 |
| Glycosaminoglycan | Heparan sulfate | Heparan sulfate |
| Buoyant Density (g/ml) | 1.3–1.35 | 1.32–1.4 |
| BM-1 Antiserum | + | + |

However, they differ in smooth muscle inhibition activity.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims

What is claimed is:

1. A smooth muscle cell growth inhibitor, comprising a substantially pure glycosaminoglycan having smooth muscle cell growth inhibition activity and being isolatable from an endothelial-cell-conditioned medium as part of a heparan sulfate proteoglycan having molecular weight of about $10^5$ to $10^7$ and a buoyant density of less than 1.4 g/ml which release a glycosaminoglycan chain having a molecular weight of about 55,000 to 75,000 on protease cleavage.

2. The inhibitor of claim 1, wherein said glycosaminoglycan comprises at least 90 weight % of molecules having a molecular weight of at least 1000 in a composition containing said inhibitor.

3. The inhibitor of claim 1, wherein said endothelial-cell-conditioned media contains cells consisting essentially of human, procaine, bovine, sheep, rabbit, rat, mouse, or monkey endothelial cells.

4. The inhibitor of claim 1, wherein said glycosaminoglycan chain has a molecular weight of about 60,000–70,000 and said proteoglycan has a buoyant density of about 1.3 g/ml and a molecular weight of about $0.8 \times 10^6$ to $1.2 \times 10^6$.

5. The inhibitor of claim 1, wherein said glycosaminoglycan has a molecular weight of about 55,000 to 75,000.

6. The inhibitor of claim 1, wherein said glycosaminoglycan has a molecular weight of about 1,000 to 55,000.

7. The inhibitor of claim 1, wherein said proteoglycan binds specifically with an antibody having specific binding affinity for a protein epitope of a basement membrane heparan sulfate proteoglycan.

8. The inhibitor of claim 7, wherein said basement membrane heparan sulfate proteoglycan is produced by EHS tumor.

9. The inhibitor of claim 1, wherein said activity is retained when said inhibitor is contacted with chondroitin ABC lyase under cleavage conditions.

10. The inhibitor of claim 1, wherein the inhibitor is soluble as an intact protoglycan in said medium in the presence of albumin or serum, and no endoglycosidic cleavage is required to release soluble glycosaminoglycan chains from endothelial cells.

11. A smooth muscle cell growth inhibitor, comprising a substantially pure heparan sulfate proteoglycan isolatable from an endothelial-cell-conditioned medium and having a molecular weight of about $10^5$ to about $10^7$, a buoyant density of less than 1.4 g/ml, glycosaminoglycan chains with an average molecular weight of about 55,000 to 75,000 on protease cleavage, and smooth muscle cell growth inhibition activity.

12. The inhibitor of claim 11, wherein said proteoglycan has a buoyant density of about 1.3 g/ml.

13. The inhibitor of claim 11, wherein said molecular weight is about $10^6$.

14. The inhibitor of claim 11, wherein said proteoglycan comprises a proteinaceous epitope recognized by an antibody specific for a basement membrane heparan sulfate proteoglycan.

15. In a method of purifying a proteoglycan smooth muscle cell growth inhibitor from a liquid medium containing said inhibitor as biochemically synthesized by endothelial cells, an improvement which comprises:
including a dialyzable detergent in said medium prior to additions of reagents which induce dissociative Or chaotropic conditions, and maintaining said detergent in the presence of said proteoglycan during said purifying.

16. The method of claim 15, wherein said purifying comprises gel filtration of an endothelium-conditioned medium.

17. The method of claim 15, wherein said purifying comprises density gradient centrifugation.

18. A method of purifying a smooth muscle growth inhibitor, which comprises:
separating endothelial cells in a growth medium from said medium to provide an endothelium-conditioned medium;
adding a dialyzable detergent to said conditioned medium; and
separating a heparan sulfate proteoglycan from other macromolecules present in said detergent-added conditioned medium.

19. The method of claim 18, wherein said separating comprises ion exchange, gel filtration, or density gradient centrifugation.

20. The method of claim 19, wherein said separating comprises density gradient centrifugation and collection of a fraction at a buoyant density of about 1.25 to 1.35 g/ml.

21. The method of claim 18, comprising gel filtration to provide a sample characterized by a molecular weight of at least 500,000.

22. The method of claim 21, further comprising density gradient centrifugation and collection of a fraction at a buoyant density of about 1.25 to 1.35 g/ml.

23. The method of claim 18, wherein said detergent is dialyzable through a semipermeable membrane have a molecular weight cutoff of 500,000 or less from a solution containing said inhibitor.

24. The method of claim 18, wherein said detergent is octylglucoside or sodium deoxycholate.

25. A method of inhibiting growth of smooth muscle cells, which comprises adding to a growth medium containing said cells an effective growth-inhibiting amount of a glycosaminoglycan or proteoglycan of claim 1.

26. The method of claim 25, wherein said amount provides a concentration of from 20 to 1000 ng/ml in a liquid medium contacting said cells.

27. The method of claim 25, wherein said growth medium is an artery or vein of a mammal.

28. The method of claim 27, wherein said adding is by intravenous injection and said amount provides a serum concentration of from 50 to 500 ng/ml.

29. The method of claim 25, wherein said growth medium is an in vitro tissue- or cell-culture medium.

* * * * *